(12) United States Patent
Knight et al.

(10) Patent No.: US 6,959,603 B2
(45) Date of Patent: Nov. 1, 2005

(54) ULTRASONIC TESTING SYSTEM AND METHOD

(75) Inventors: Ray Knight, Houston, TX (US); Jim Wells, Houston, TX (US)

(73) Assignee: Cooper Cameron Corporation, Houston, TX (US)

( * ) Notice: Subject to any disclaimer, the term of this patent is extended or adjusted under 35 U.S.C. 154(b) by 0 days.

(21) Appl. No.: 10/770,146

(22) Filed: Feb. 2, 2004

(65) Prior Publication Data

US 2004/0148730 A1 Aug. 5, 2004

Related U.S. Application Data

(62) Division of application No. 09/727,130, filed on Nov. 29, 2000, now Pat. No. 6,684,706.

(51) Int. Cl.[7] .............................................. G01N 29/10
(52) U.S. Cl. ....................................................... 73/623
(58) Field of Search .......................... 73/623, 601, 628, 73/866.5

(56) References Cited

U.S. PATENT DOCUMENTS

| | | | | |
|---|---|---|---|---|
| 3,786,684 A | * | 1/1974 | Wiers et al. | ................ 73/866.5 |
| 5,467,640 A | | 11/1995 | Salinas | |
| 5,591,912 A | * | 1/1997 | Spisak et al. | .................. 73/623 |
| 5,992,246 A | * | 11/1999 | Nice | ........................... 73/623 |

FOREIGN PATENT DOCUMENTS

| | | |
|---|---|---|
| EP | 0736722 A1 | 10/1996 |
| EP | 0754902 A3 | 12/1998 |
| GB | 2242497 A | 10/1991 |
| GB | 2255815 A | 11/1992 |
| GB | 2336913 A | 11/1999 |

* cited by examiner

Primary Examiner—John E. Chapman
(74) Attorney, Agent, or Firm—Law Office of Tim Cook P.C.

(57) ABSTRACT

A comprehensive system for the cleaning, inspection, and testing of tubulars, particularly riser pipes, is provided. In a first aspect, a method of inspecting a tubular comprises cleaning, visually inspecting, corrosion mapping, and TOM testing the tubular. In another aspect, a specially designed or adapted tool is provided for each of the steps of the method.

6 Claims, 11 Drawing Sheets

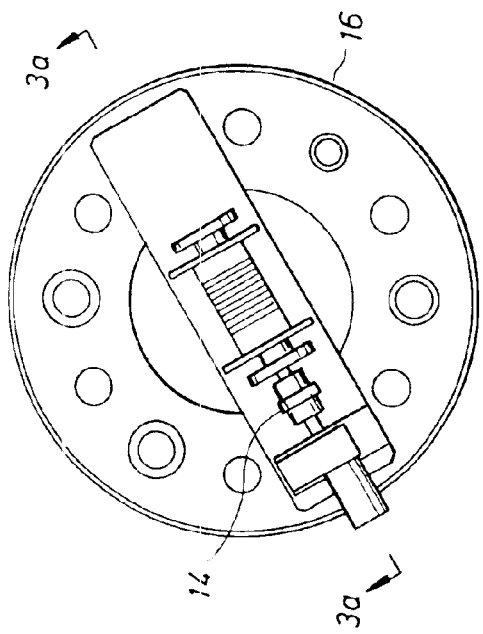
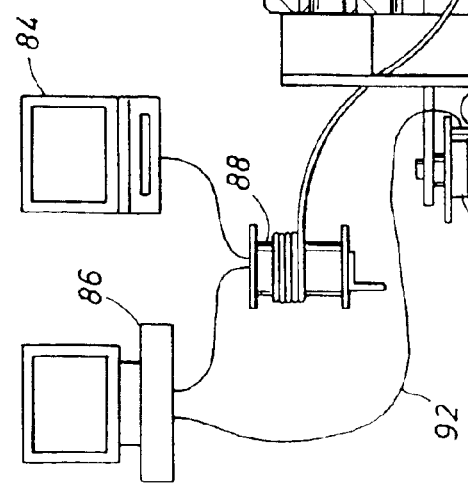
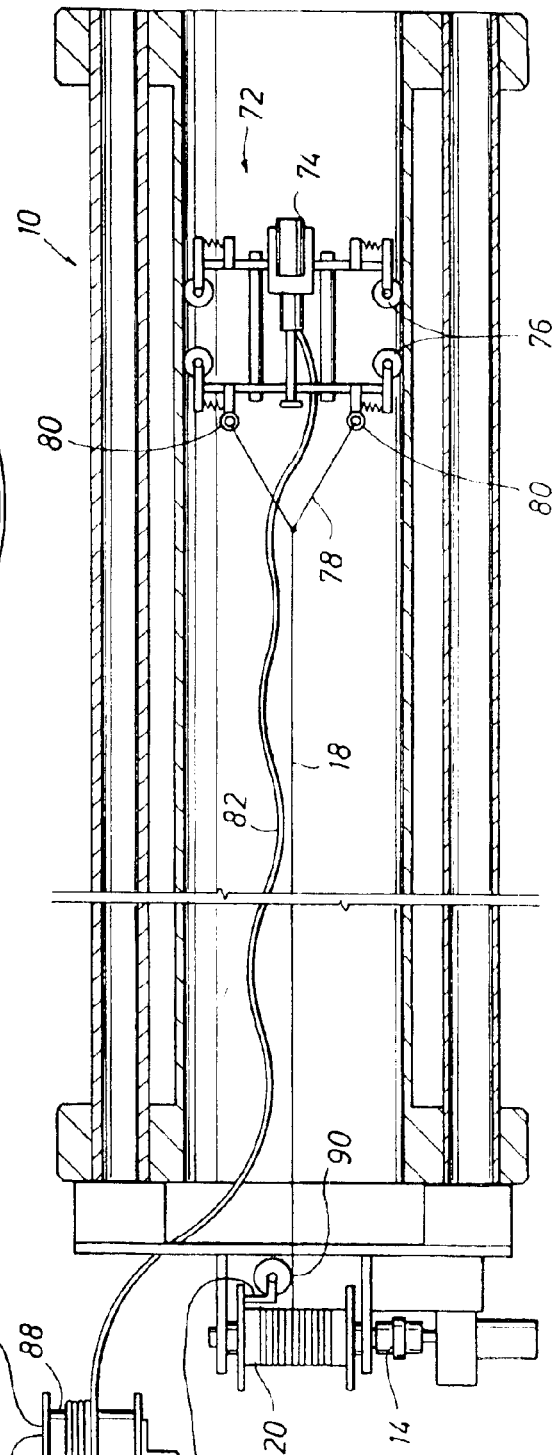
FIG. 3a
FIG. 3b

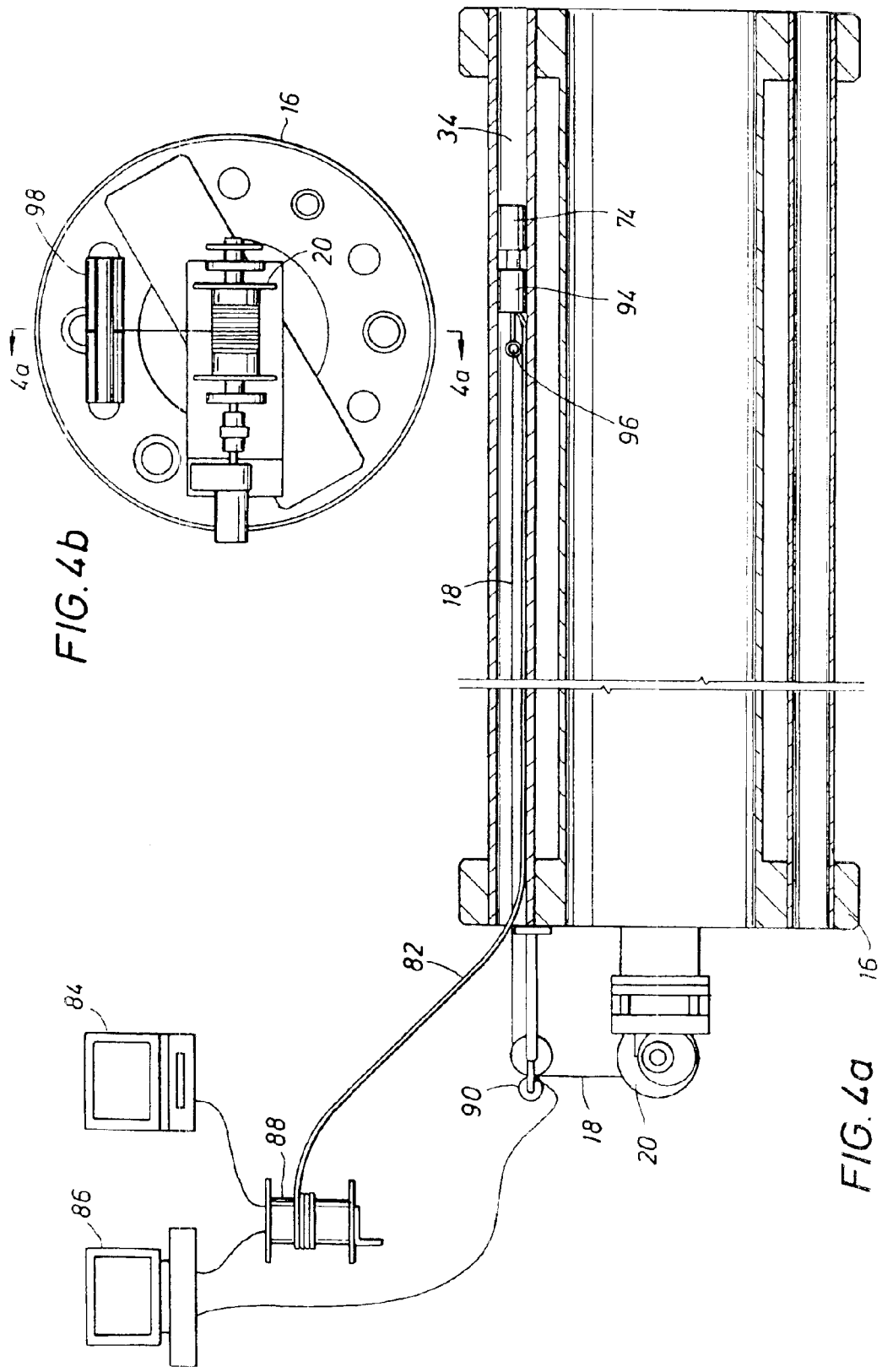

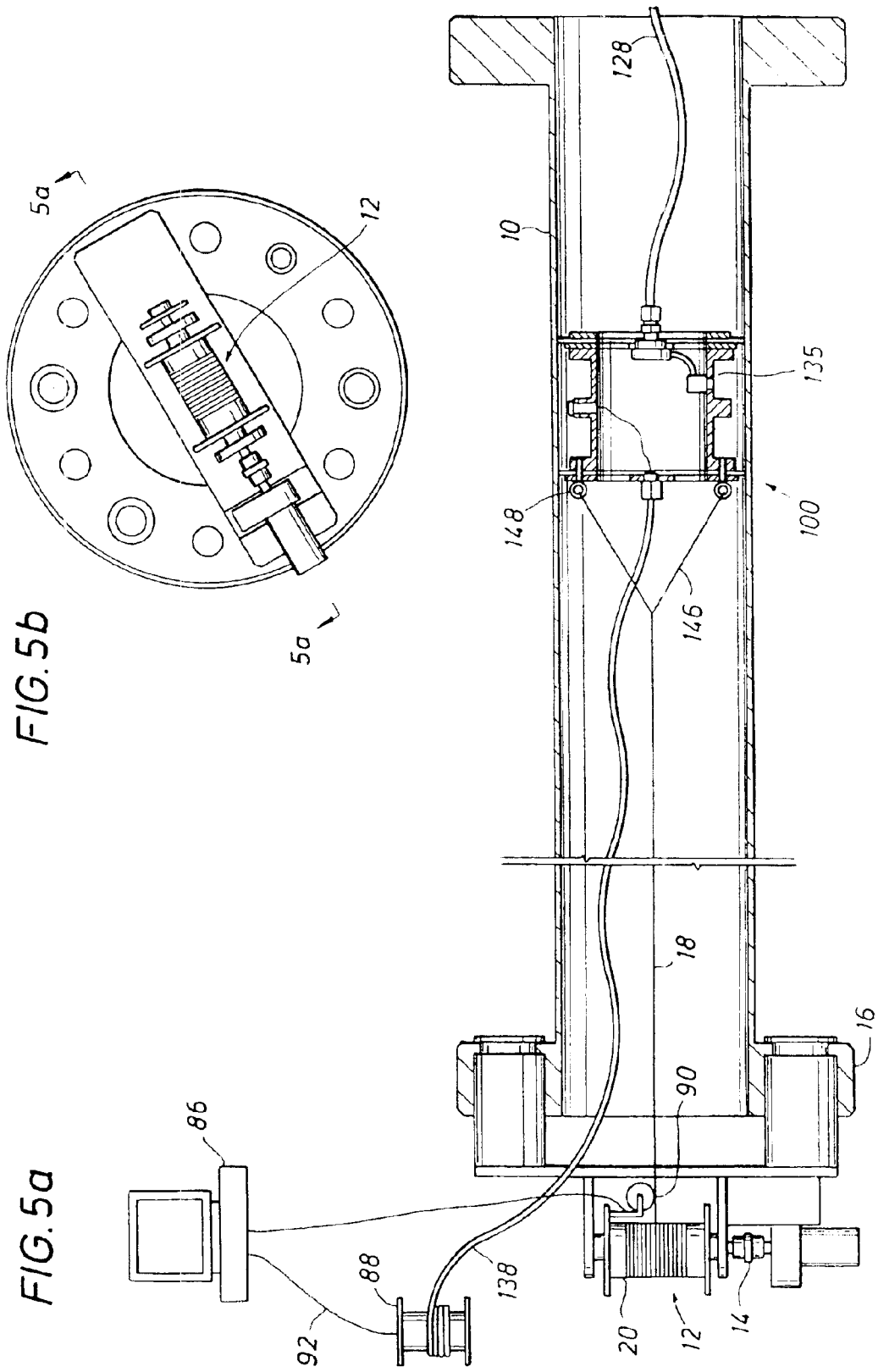

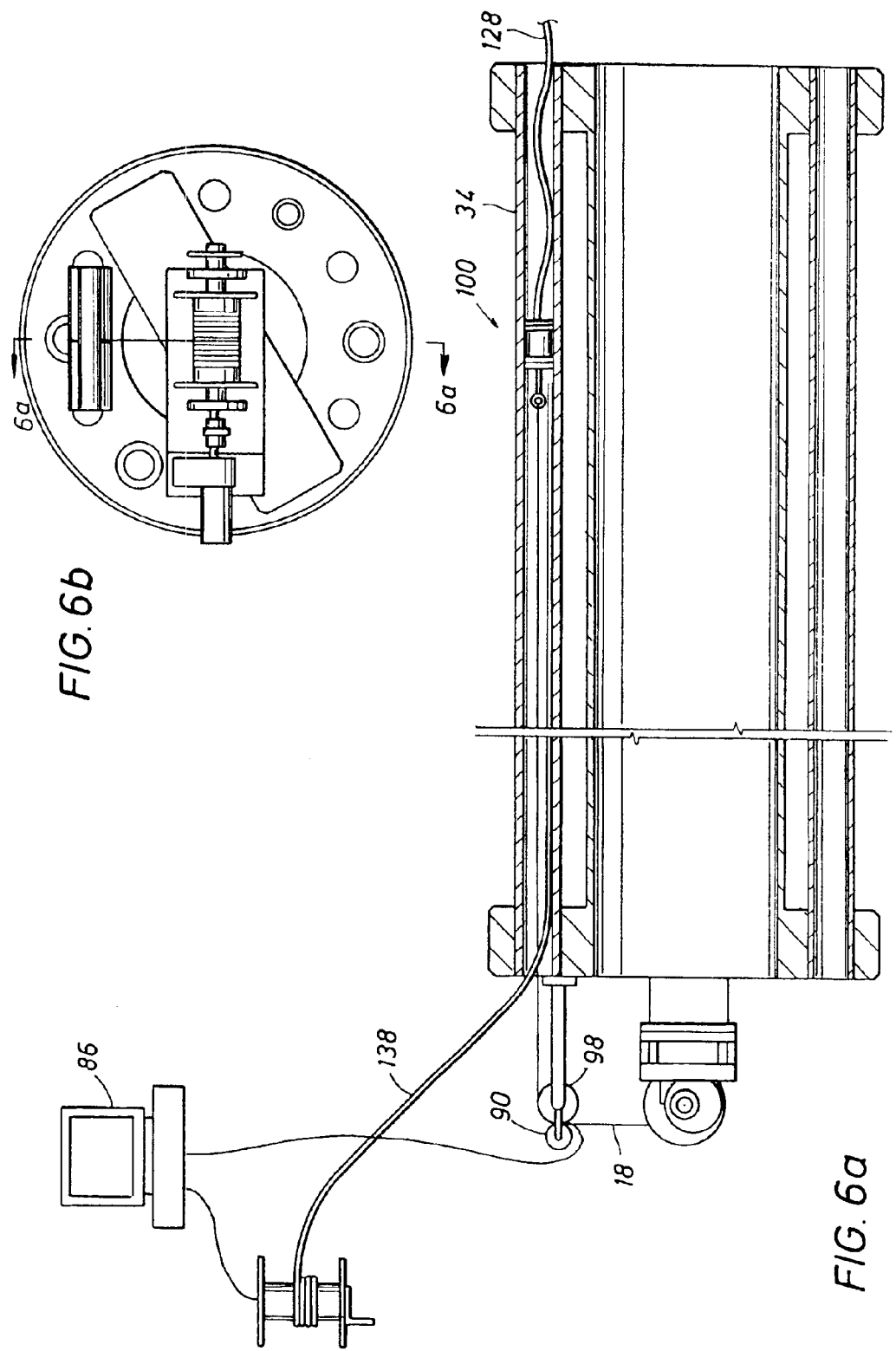

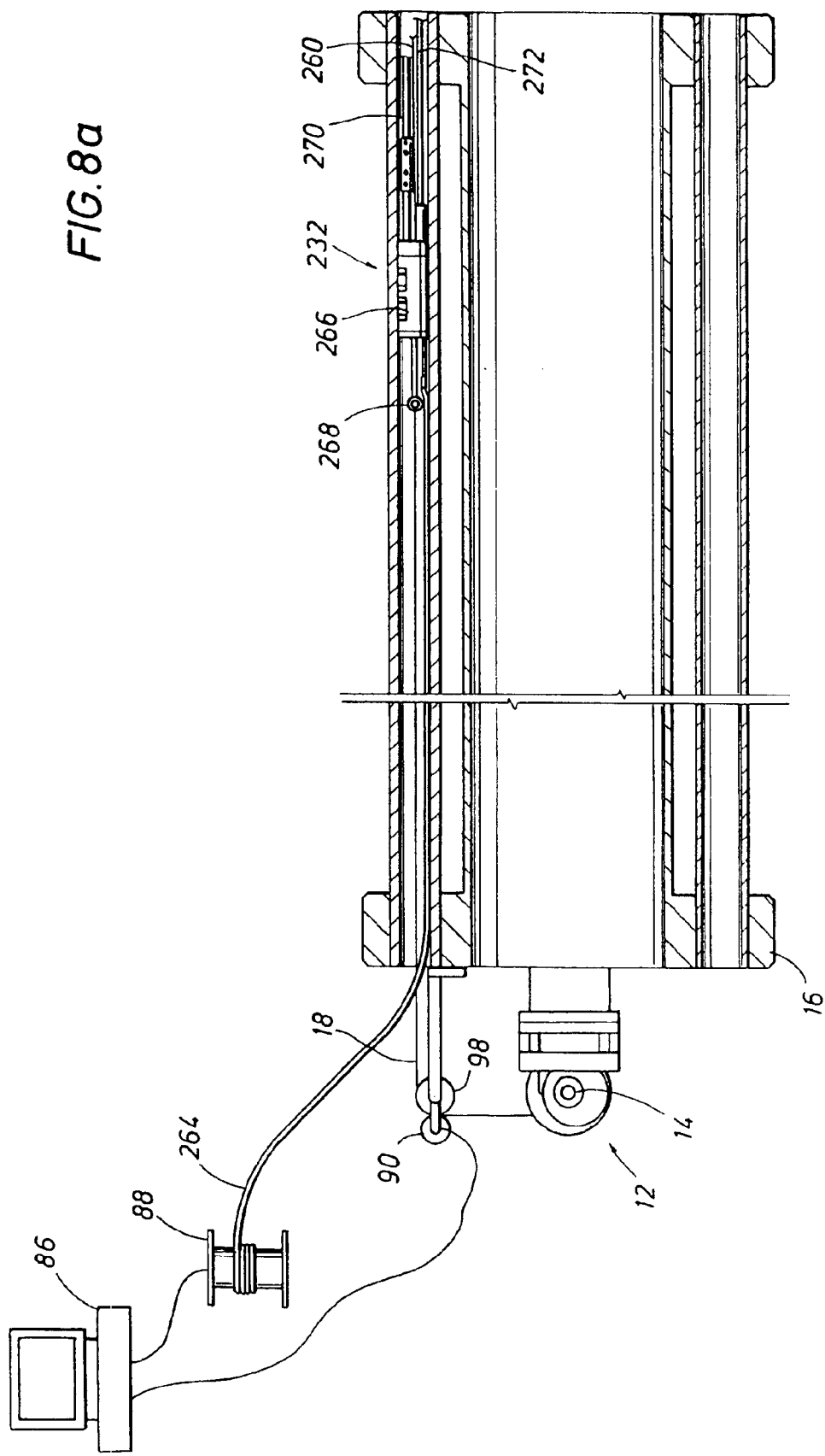

ULTRASONIC TESTING SYSTEM AND METHOD

This is a Division of U.S. patent application Ser. No. 09/727,130 filed Nov. 29, 2000, now U.S. Pat. No. 6,684,706.

FIELD OF THE INVENTION

The present invention relates generally to the field of non-destructive testing and, more particularly, to a method and apparatus for cleaning and inspecting tubulars, including inspecting for flaws in pipe sequentially using pulse echo and time of flight diffraction (TOFD).

BACKGROUND OF THE INVENTION

There has long been a need for methods of cleaning and inspecting tubulars, particularly offshore riser pipe, on site. Typical methods used today include disassembling the riser pipe from a rig, transporting the riser pipe to a yard, and there conducting inspection and testing of the tubular using well known techniques. Such a method is not only expensive and time consuming, but also very disruptive of normal operations on the rig.

Thus, there remain a need for a system and method of inspecting tubulars on site to minimize down time of the rig, and to save the costs of transporting and returning the tubulars under inspection.

Even the techniques used at the yard for the testing and inspection of tubulars have certain drawbacks. Various techniques have been developed to detect flaws in structures, particularly welds in such structures. The ability to detect flaws in structures such as tubulars in drilling and production rigs and pipelines is especially critical before any catastrophic failure occurs.

Ultrasonic testing of metal structures has proved to an effective and practical tool for nondestructive testing (NDT). Known ultrasonic techniques typically yield reliable examination results. However, some geometries make known ultrasonic techniques difficult or even impossible to apply, or yield inaccurate results.

One technique that has gained common acceptance in the NDT field is referred to as the echodynamic technique. This technique consists of measuring the duration of the defect echo in axial or circumferential tube direction when the ultrasonic probe (in pulse-echo mode) is moved over the defect. Such a defect may involve slag, porosity, stress cracking, or other anomalies from the anticipated metal grain structure. In the pulse-echo mode, the depth of a defect is calculated from the probe displacement distance at which a defect echo was picked up. To detect the defect, the amplitude of the defect echo should be above noise level. However, many defects that are of particular concern escape detection if they are oriented in a particular way relative to the applied pulse echo, because this technique relies on the reflectivity of the defect. In fact, the pulse echo technique is used in the present invention for corrosion mapping in determining pipe wall thickness. However, as previously described, the pulse echo technique may miss certain flaws, and this fact has lead to the development of other testing techniques.

The Time of Flight Diffraction technique (TOFD) was developed by the AEA's Harwell Laboratory in Britain in the mid seventies as a method of accurately sizing and monitoring the through-wall height of in-service flaws in the nuclear industry. For weld inspection, it was quickly recognized that the method was equally effective for the detection of flaws, irrespective of type or orientation of the flaw, since TOFD does not rely on the reflectivity of the flaw. Rather, TOM detects the diffracted sound initiating from the tips of the flaw.

In TOFD, a transmitting probe emits a short burst of sound energy into a material and the sound energy spreads out and propagates in an angular beam. Some of the energy is reflected from the flaw but some of the energy is incident to the flaw and is diffracted away from the flaw. A fraction of this diffracted sound travels toward a receiving probe. The diffracted signals which are received by the receiving probe are time resolved using simple geometry calculations and are graphically displayed in a grey scale form.

While the TOFD technique has proved effective for many geometries, there remains a need for a method and system for detection of flaws from within a cylindrical structure, such as a pipe or riser stanchion. The present invention is believed to be the first structure and method of NDT using TOFD from within a tubular such as a riser pipe.

SUMMARY OF THE INVENTION

The present invention addresses these and other needs in the non-destructive testing art by providing a comprehensive system for the cleaning, inspection, and testing of tubulars, particularly riser pipes. In a first aspect of the present invention, a method of inspecting a tubular comprises cleaning, visually inspecting, corrosion mapping, and TOFD testing the tubular. The present invention is also adapted for use with new construction in which the cleaning step may not be necessary in some cases. In another aspect of the invention, a specially designed or adapted tool is provided for each of the steps of the method.

The step of cleaning the inside of the tubular includes pre-wetting, if desired, to remove loose debris and to soften dried drilling fluids and other materials. An air motor driven wire brush with an alignment tool is then pulled or pushed through the tubular. For small lines, which may include weld material protruding into the cylindrical space, a cutting tool is also provided to precede the wire brush. The wire brush may also be followed by a jet spray of water to wash away cuttings, rust, and dust.

The step of visual inspection comprises moving a camera throughout the tubular. A digital linear placement transducer, referred to as an encoder, is provided to precisely locate the camera within the tubular. The camera provides a video signal to a computer and to a recorder for a permanent record.

The step of corrosion mapping employs a pulse echo system to map wall thickness of the tubular. A drive system is provided to move the tool holding the pulse echo probes through the tubular, and the computer once again makes a record of the mapping. Finally, a TOM system is provided to detect flaws in the tubular seam and girth welds, such as inservice defects, stress and fatigue cracking, corrosion, erosion, weld fabrication defects, lack of fusion (LOF), slag porosity, and other defects.

These and other features of the invention will be apparent to those skilled in the art from a review of the following description along with the accompanying drawings.

BRIEF DESCRIPTION OF THE DRAWINGS

FIG. 1b is an end view of the cleaning system of FIG. 1a.

FIG. 3a is a side view in partial section of a system for the visual inspection of the larger diameter pipe.

FIG. 3b is an end view of the visual inspection system of FIG. 3a.

FIG. 4a is a side view in partial section of a system for the visual inspection of small ID pipe, such as for a 3" or 4" nominal ID pipe.

FIG. 4b is an end view of the visual inspection system of FIG. 4a.

FIG. 5a is a side view in partial section of a system for performing corrosion mapping inspection of a large diameter pipe.

FIG. 5b is an end view of the system of FIG. 5a.

FIG. 6a is a side view in partial section of a system for performing corrosion mapping inspection of a small diameter tubular.

FIG. 6b is an end view of the system of FIG. 6a.

FIG. 8a is a side view in partial section of a preferred system for performing TOFD testing of a small diameter tubular.

FIGS. 8b and 8c are side section views of TOFD tools for performing testing of 4" and 3" tubulars, respectively, suitable for use with the system of FIG. 8a.

DETAILED DESCRIPTION OF PREFERRED EMBODIMENTS

The present invention includes a system for the inspection of tubulars and a method of conducting such an inspection using the system. The system of the invention includes the systems for carrying out the various stages of inspection, as well as the tools which have been designed or specially adapted for the inspection. The method of the invention comprises primarily four steps: (1) cleaning; (2) visual inspection; (3) corrosion mapping; and (4) TOFD inspection. The following description follows through the four steps of the method, with the structure described during each step.

Cleaning

Figure 1A:
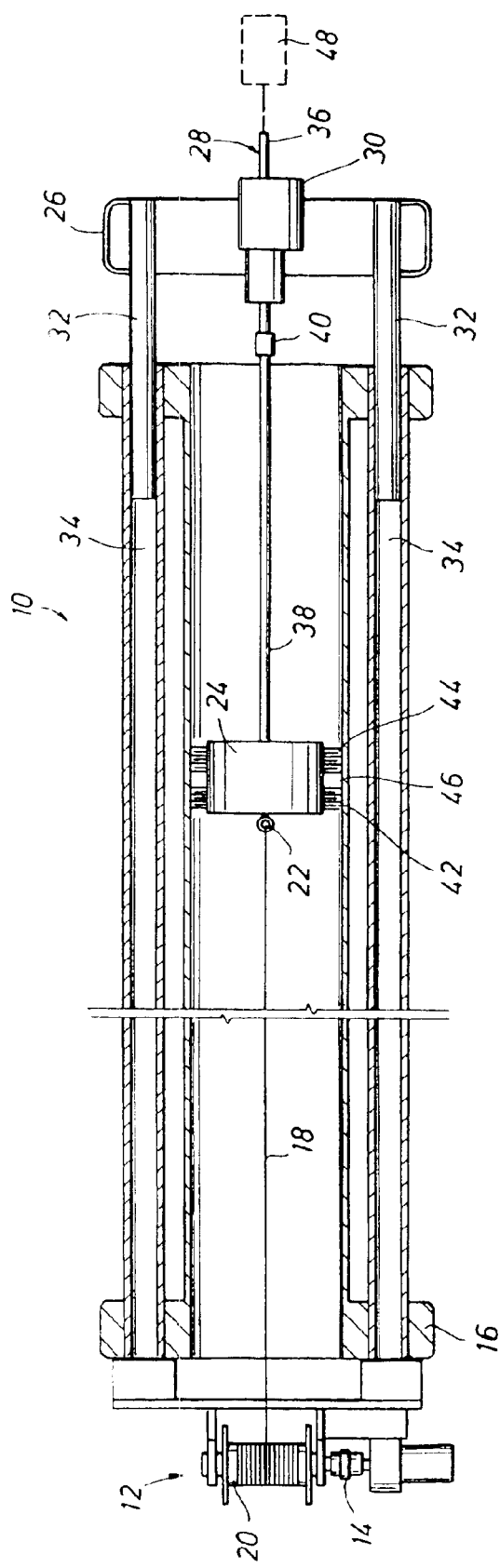
FIG. 1a is a side view in partial section of a cleaning system in accordance with this invention for cleaning a large ID pipe, such as a 21" ID main riser pipe.
Figure 1B:
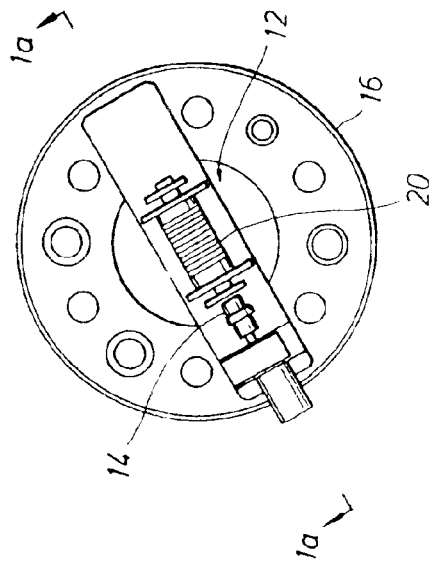

FIGS. 1 and 1a show the arrangement for cleaning the main, 21" ID riser pipe 10. At one end of the pipe 10 is coupled a winch assembly 12 driven by a winch motor 14 and the winch assembly 12 is adapted for mounting to a flange 16 of the pipe 10. A wire line 18 is wound on a winch spool 20, enough wire line to reach the entire length of the pipe 10. The end of the wire line 18 terminates in a swivel 22, which couples to a cleaning tool 24. As used herein, the term "drawing system" refers to the mechanism for drawing the cleaning tool through the pipe, and includes the winch assembly 12, the winch motor 14, and the wire line 18.

On the opposite end of the pipe 10 is mounted a drive mechanism 26 to actuate the cleaning tool 24. The drive mechanism 26 includes a motor mount 28 on which is mounted an air motor 30. The motor mount 28 also includes at least two guide bars 32 which slidingly extend into auxiliary lines 34 and the guide bars are preferably about 3.5 feet long. The air motor 30 is provided with an air supply 36, which may be any available air supply of about 120 psi. Coupled to the drive shaft of the air motor is a drive tube 38, which is preferably made up of 3' sections, and the sections of drive tube 38 may be quickly and easily made up with couplings 40. The end of the drive arm or tube 38 opposite the drive motor 30 is coupled to the cleaning tool 24. The cleaning tool 24 includes a pair of wire brushes 42 and 44, separated by a centralizer ring 46, which maintains the cleaning tool in alignment within the pipe 10 to ensure complete circumferential cleaning of the inside of the pipe. Finally, speed control for the air motor 30 is provided by an air regulator and dryer 48 for complete control of the cleaning operation.

To begin the procedure of cleaning the inside of the main pipe 10, the inside of the pipe is first flushed, preferably with potable water, to remove loose debris and to pre-wet any dried drilling mud for ease of removal by the cleaning tool 24. Next, the motor mount 28 is installed by sliding the guide bars into the auxiliary tubes. With the guide bars fully inserted, the position of the air motor can be adjusted to center the axis of rotation of the motor output shaft to account for variations in the positioning of the auxiliary pipes. The mounting assembly is then pulled back out (about 3.5 feet), and the first section of drive tube 38 is installed on the motor drive. This provides sufficient clearance for the cleaning tool 24 on the end of the first section of drive tube 38. The cleaning tool is then placed inside the end of the main pipe 10. Next, the air line 36 is connected to the motor and the air regulator 48 is adjusted to zero. The air pressure is then slowly increased until the cleaning tool 24 just starts to turn. Note that due to the coefficient of friction, more air pressure will be required to start turning the tool than is required to keep the tool turning.

The cleaning tool can then be manually run into the pipe for cleaning the first portion. Alternatively, the wire line 18 can be pushed through the pipe 10 and connected to the swivel 22 prior to making up the tool to the air motor. With this setup, the winch motor is used to pull the cleaning tool through the pipe. When the motor mount 28 contacts the end of the pipe, the air supply 36 is shut off, and the mount 28 is pulled back to provide enough clearance to attached another 3' section of drive tube 38. The procedure is repeated until the entire length of the pipe 10 has been cleaned with the cleaning tool. The process is completed by flushing the pipe with water until the water at the other end of the pipe is clear of debris.

Figure 2:
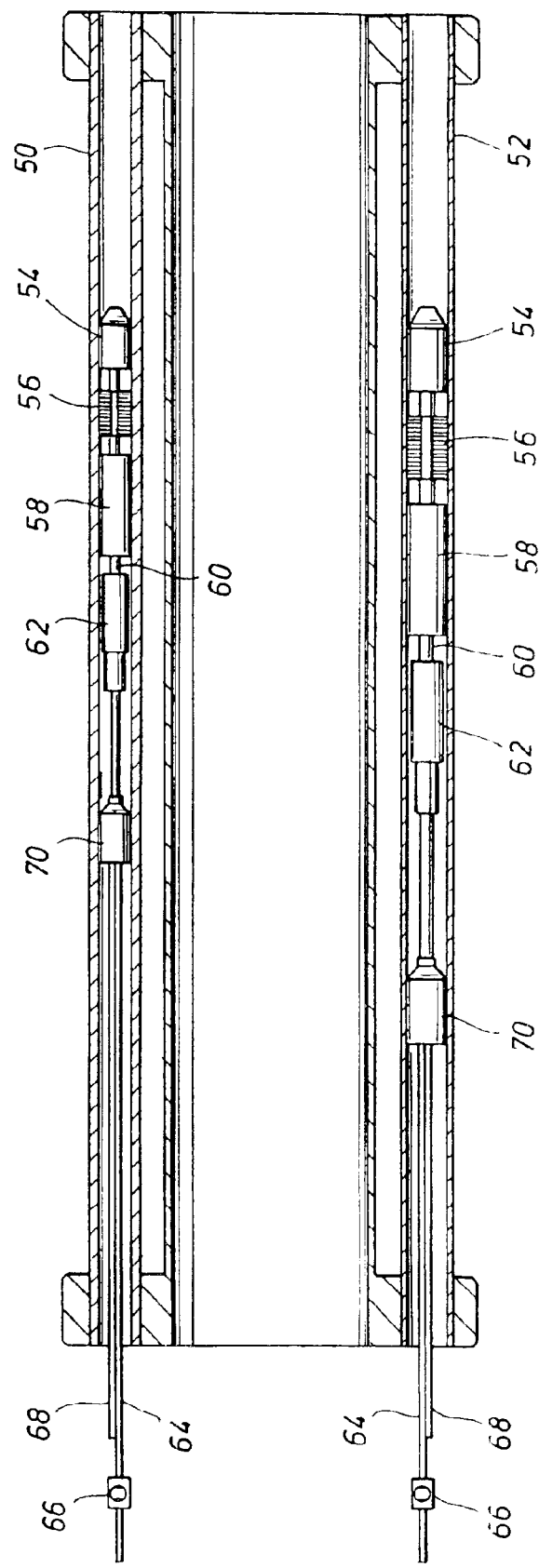
FIG. 2 is a side view in partial section of a cleaning system for cleaning smaller ID pipe, such as 3" and 4" pipes.

Another setup is required for cleaning the smaller auxiliary pipes. FIG. 2 depicts the arrangement for cleaning such smaller diameter 3 and 4 inch nominal ID pipes, which may otherwise be referred to herein as tubulars or lines. These are, for example, a choke and kill line 50 and a mud booster line 52, respectively. A similar arrangement is used for cleaning both lines, and the cleaning tool comprises a cutting or grinding tool 54 which is used primarily to remove welds which extend down into the lines 50 and 52. Removing the protruding welds ensures that the inspection tools which are later to be used have room to travel freely through the pipes.

Immediately behind the cutting tool 54 is a wire brush 56 for removing rust and loose debris from the inside of the pipe. Immediately behind the wire brush 56 is a centralizing sleeve 58, preferably made of a hard plastic or other appropriate material, to align the cutting tool 54 and the wire brush 56. The cutting tool, wire brush, and centralizing sleeve are all coaxially mounted to a drive shaft 60 which is coupled to an air motor 62 for high speed rotation of the coaxially mounted tools. The air motor 62 is provided with pressurized air from a rig air supply line 64 which is provided with a valve 66 which provides both positive shutoff and speed control by controlling air pressure to the air motor 62. On a common line with the rig air supply line 64 is a water supply line 68 which provides water under pressure to water jet nozzle 70 which washes rust, dust, and other debris forward through the pipe.

Visual Inspection

FIGS. 3a and 3b depict a structure for visual inspection of the interior surface of the main pipe 10. An alternative means for visual inspection uses a camera mounted on a TOM tool, described below.

The structure of FIG. 3a includes a camera carrier 72 on which is mounted a camera 74 having a wide angle lens for complete circumferential viewing of the interior of the pipe. The carrier 72 is retained securely centered within the pipe 10 with a plurality of spring loaded wheels 76. The carrier with camera mounted thereon is drawn through the pipe with a harness 78 coupled to the carrier with swivel mounts 80. The harness 78 is joined to the wire line 18 wound onto the winch 20 spool, as previously described.

The camera 74 provides a signal over a signal line 82 to a television and video cassette recorder 84 and a computer 86 to provide real time viewing of the camera view and to provide a record of the visual inspection. The signal line 82 is preferably taken up on a take-up reel 88 to keep the slack out of the signal line 82 during the inspection. As the wire line 18 is taken up by the winch, it passes through a digital linear placement transducer or encoder 90, which is simply an idler of precisely known diameter so that the position of the carrier 72 along the longitudinal direction of the tubular is known. The encoder 90 is coupled to the computer 86 by a signal line 92. The encoder may alternatively be mounted to the carrier 72, and the signal line 92 may then be included with the signal line 82.

Because of constricted space, a different structure is called for when viewing the interior surface of the smaller lines 34, as depicted in FIGS. 4a and 4b. A similar arrangement is provided for the inspection of both 3" and 4" lines. The system of FIGS. 4a and 4b uses the same mounting for the winch as previously described, but now it can be seen that the winch is rotatable on its mount so that the wire line 18 may be directed onto a line 34.

The camera 74 is mounted to a centralizer sleeve 94, which is coupled to the wire line 18 with a swivel mount 96. The centralizer sleeve adapts the same camera to different ID auxiliary lines. The signal from the camera 74 is provided over the signal line 82 to the television and recorder 84 and to the computer 86 as previously described. The camera is drawn through the auxiliary line 34 by the wire line, which passes over the encoder 90 so that the longitudinal position of the camera is known at all times. The wire line passes over an idler pulley 98 which presses against the encoder 90.

The purpose of the visual inspection of the interior surface is to show up any obvious surface cracks or corrosion, and to provide for a more comprehensive ultrasonic inspection to follow. It provides the user with a visual inspection record, through the recorder 84, of the assembled drilling riser joint internal pipe surfaces, for example, although the system and method of this invention may be applicable to other tubulars.

To use the visual inspection system, the camera is installed to the appropriate size adapter sleeve for the line to be inspected, and the camera cable is fished through the line, starting from the box end to the pin end, for example. The cable is then connected to the camera, and the winch assembly is mounted to the end of the riser pipe. The wire line is coupled to the encoder, and the remaining cable connections are made to the computer and television with recorder. The encoder is zeroed, and the image is viewed on the screen of the television to ensure adequate picture quality. Then, using the winch, the wire line is drawn through the tubular. The user can watch the television while making an inspection record. The procedure should then be repeated for all tubulars to be inspected.

Corrosion Mapping

Figure 5C:
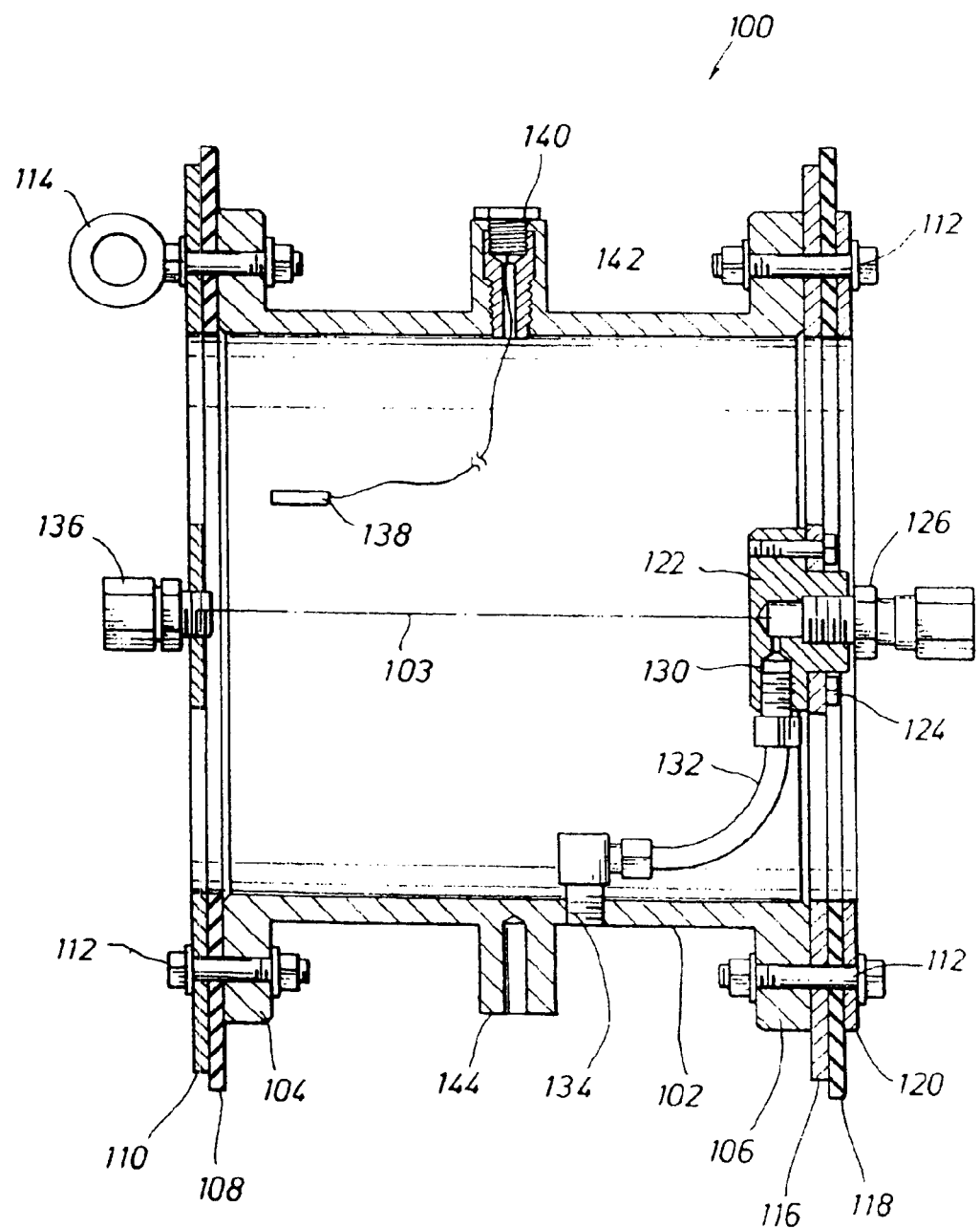
FIG. 5c is a side section view of corrosion mapping tool suitable for use in the inspection system of FIGS. 5a and 5b.

FIGS. 5a, 5b, and 5c depict the structure for corrosion mapping of the interior of the main pipe 10. FIG. 5a is a side view of a corrosion mapping tool 100, constructed in accordance with the invention, positioned within the main pipe 10. FIG. 5b is an end view showing the mounting hardware for moving the tool 100, and FIG. 5c is a detail view of the corrosion mapping tool 100 itself.

Referring first to FIG. 5c and the corrosion mapping tool 100, the tool comprises primarily a truncated cylinder 102 with flanges 104 and 106 at the left and right ends of the cylinder 102, respectively. The cylinder 102 is axially oriented along an axis 103, which when in use is coaxial with the axis of the pipe 10. Mounted to the flange 104 in abutting contact is a seal plate 108 which is retained by an end plate 110, held to the flange with a set of bolts 112, for example. One such bolt 112 may be replaced by a lifting eye 114 to assist in transporting the tool 100, since the tool 100 is roughly 20" in diameter and quite heavy. At the other end of the cylinder 102, mounted to the flange 106, is an end plate 116, a seal plate 118, and a backing support ring 120, all held to the flange 106 with a set of bolts 112, for example.

Note that the mounting hardware for the seal plates 108 and 118 is not the same for each seal plate. The end plate 110 is to the left of the seal plate 108, i.e. away from the flange 104, and the end plate 116 is to the left of the seal plate 118, i.e. in abutting contact with the flange 106. This arrangement provides support for the compliant seal plates when the bend under friction against in the inside diameter of the pipe 110 when the tool 100 is drawn through the pipe.

The end plate 116 also provides a mount for a hub 122 held to the end plate 116 with a plurality of bolts 124, for example. The hub receives a coupling 126, which receives a water hose connection 128 (see FIG. 5a). Water from the water hose connection 128 provides a couplant for the pulse echo signal used in the corrosion mapping as described below. The hub 122 also includes a water channel 130 leading the flow of water to a flexible tube 132 which carries the water to a penetration 134 through the cylinder 102. Thus, the water floods an annular chamber 135 (See FIG. 5a) formed by the cylinder 102, the seal plates 108 and 118, and the interior diameter of the main pipe 10.

The end plate 110 provides a mount for a cable connector 136 which receives a transducer signal cable 138 (See also FIG. 5a) to be described below. The transducer signal cable 138 terminates in a pulse echo transducer 140, which is mounted in an insert 142 which in turn is installed in the cylinder 102. It should be understood that although only one transducer is shown, a plurality of transducers are used in order to provide a full 360° coverage to map the entire pipe. The transducer 140 provides a pulse echo signal to determine wall thickness of the cylinder 102 in a manner well known in the art. The cylinder 102 may also provided with a nipple 144 to receive a lifting ring, if desired.

FIGS. 5a and 5b show the arrangement for the use of the tool 100. As previously described with regard to the cleaning of the pipe 10, the winch assembly 12 is mounted at one end of the pipe 10 and the winch assembly is mounted to the flange 16. The winch is driven by a winch motor 14 and includes a winch spool 20 upon which is wound a wire line 18, enough wire line to reach the entire length of the pipe 10. The end of the wire line 18 terminates in a harness 146, which couples to the tool 100 with a set of swivels 148.

The transducer 140 provides a signal over the signal line 138 (which may be the same signal line 82 as previously described) to the computer 86 to provide a record of the corrosion mapping inspection. The signal line 82 is preferably taken up on the take-up reel 88 to keep the slack out of the signal line 82 during the inspection. As the wire line 18 is taken up by the winch, it passes through the encoder 90 as before. The encoder provides position of the tool 100 along the longitudinal direction of the main pipe 10. The encoder 90 is coupled to the computer 86 by the signal line 92. The encoder may alternatively be mounted to the carrier 100, and the signal line 92 may then be included with the signal line 82.

To use the tool 100, the wire line 18 and the signal line 138 are fed through the length of the pipe 10. The winch assembly 12 is then mounted to the flange 16 and the tool is hooked up to the signal line 138 and the connecting hose 128. The tool 100 is placed flush with the end of the pipe 10, and the encoder is zeroed. Water is then applied through the hose connection 128, filling the annular chamber 135. The winch motor is then turned on, pulling the tool 100 the entire length of the pipe 10 and the position of the tool 100 is known at all times from the encoder. The transducer provides a measurement of wall thickness of the entire pipe 10, which is recorder by the computer 86 for later review and analysis.

Figure 6C:
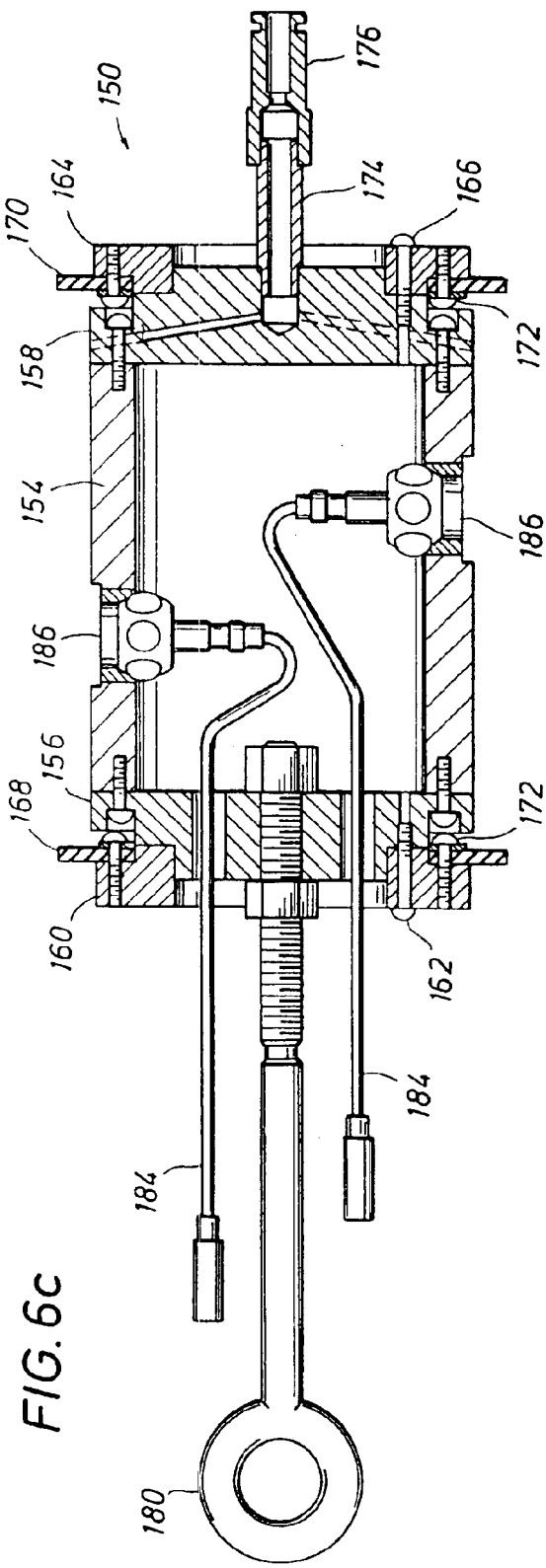
FIGS. 6c and 6d are side section views of corrosion mapping tools for 3" and 4" nominal ID tubulars, respectively, suitable for use in the system of FIGS. 6a and 6b.
Figure 6D:
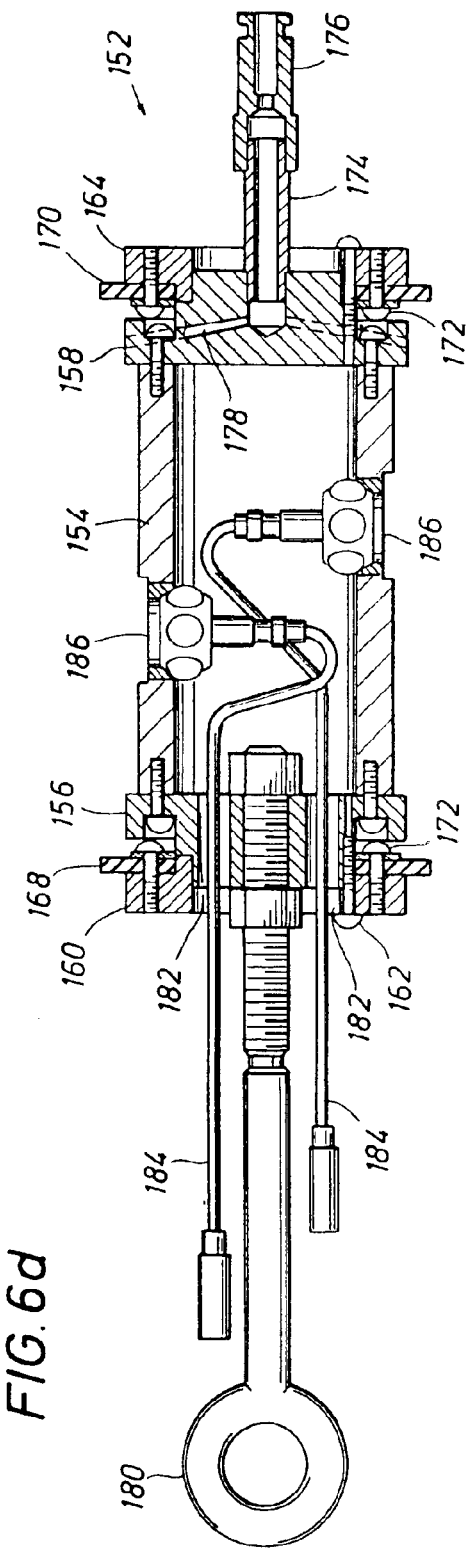

A similar arrangement is used for the corrosion mapping of the smaller tubulars, as shown in FIGS. 6a, 6b, 6c, and 6d. Referring first to FIGS. 6c and 6d, and preferred tool for corrosion mapping of the 3" and 4" tubulars are shown. A tool 150 is adapted for use in 4" nominal ID tubulars, and a tool 152 is adapted for use in 3" nominal ID tubulars. The tools contain the same components, which are numbers the same in FIGS. 6c and 6c. Thus, the following detailed description applied to both tools.

The tool (either 150 or 152) comprises primarily a cylindrical body 154, a left end cap 156, and a right end cap 158. A seal retaining ring 160 is mounted to the left end cap 156 with a set of bolts 162, for example, and a seal retaining ring 164 is mounted to the right end cap 158 with a set of bolts 166 for example. The seal retaining ring 160 holds a seal plate 168 in place, and similarly the seal retaining ring 164 holds a seal plate 170 in place. The seal retaining rings 160 and 164 are preferably secured to their respective retaining rings by a set of bolts 172.

The right end cap 158 provides a mount for a nipple 174 and a hose connector 176, providing a connection for the water source or hose connection 128. When pressurized, water flows through the nipple 174 into a set of flow channels 178 to flood the chamber formed by the seal rings, the cylindrical body, and the wall of the tubular. This provides a signal couplant for the pulse echo for the corrosion mapping tool.

The left end cap 156 provides a mount for a two ring 180 to provide a means for pulling the tool through the tubular. The left end cap 156 includes penetrations 182 through which pass signal cables 184 to carry the ultrasonic test signal from the tool. The signal cables 184 terminate at transducers 186, which are mounted in penetrations through the cylindrical body 154. It should be understood that enough transducers are provided for a complete 360° coverage around the circumference of the tubular.

FIGS. 6a and 6b illustrate the use of the tool. The system of FIG. 6a uses the same mounting for the winch as previously described, and the winch is rotatable on its mount so that the wire line 18 may be directed onto the tubular 34. The tool 100 is drawn through the tubular 34 by the wire line, which passes over the encoder 90 so that the longitudinal position of the tool 100 is known at all times. The wire line passes over an idler pulley 98 which presses against the encoder 90.

To use the corrosion mapping tool 100, the wire line 18 and the signal cable 138 are fed down through the tubular 34 to the end, where the tool 100 is attached. The tool is then coupled to the wire line and signal cable, and the hose connection 128 is attached. The tool is registered with the end of the tubular, and the encoder is zeroed. With water pressure supplied by the hose connection 128 to provide a couplant for the transducers, the tool is drawn all the way through the tubular, measuring wall thickness and providing measurements to the computer.

Time of Flight Diffraction Inspection

The tool for performing Time of Flight Diffraction (TOFD) is not described in detail, because the tool may be acquired from ScanTech, 1212 Alpine Suite A, Longview Tex. 75606. Further, the TOM technology itself was adapted from techniques provided by AEA Technology plc, whose registered office is at 329 Harwell, Didcot, Oxfordshire OX11 ORA, United Kingdom. The technique will be described in sufficient detail for a complete understanding of the present invention.

In summary, the TOM scanner system includes a very maneuverable crawler unit with four, large diameter rare earth magnetic wheels. The magnetic wheels grip the interior surface of the pipe 10 so that the crawler can be guided the entire length of the pipe. The crawler is remotely steered by the user, and the wheels include surface conforming suspension. The crawler is motor driven, and the motor is preferably a water shielded, hightorque, rare earth electric motor. All wiring, including control signals and inspection signal cables are shielded. The encoder, previously described, is preferably enclosed within the crawler for precise position measurement and indication. The TOM transducers are doublegimbaled for a fill range of motion.

Figure 7:
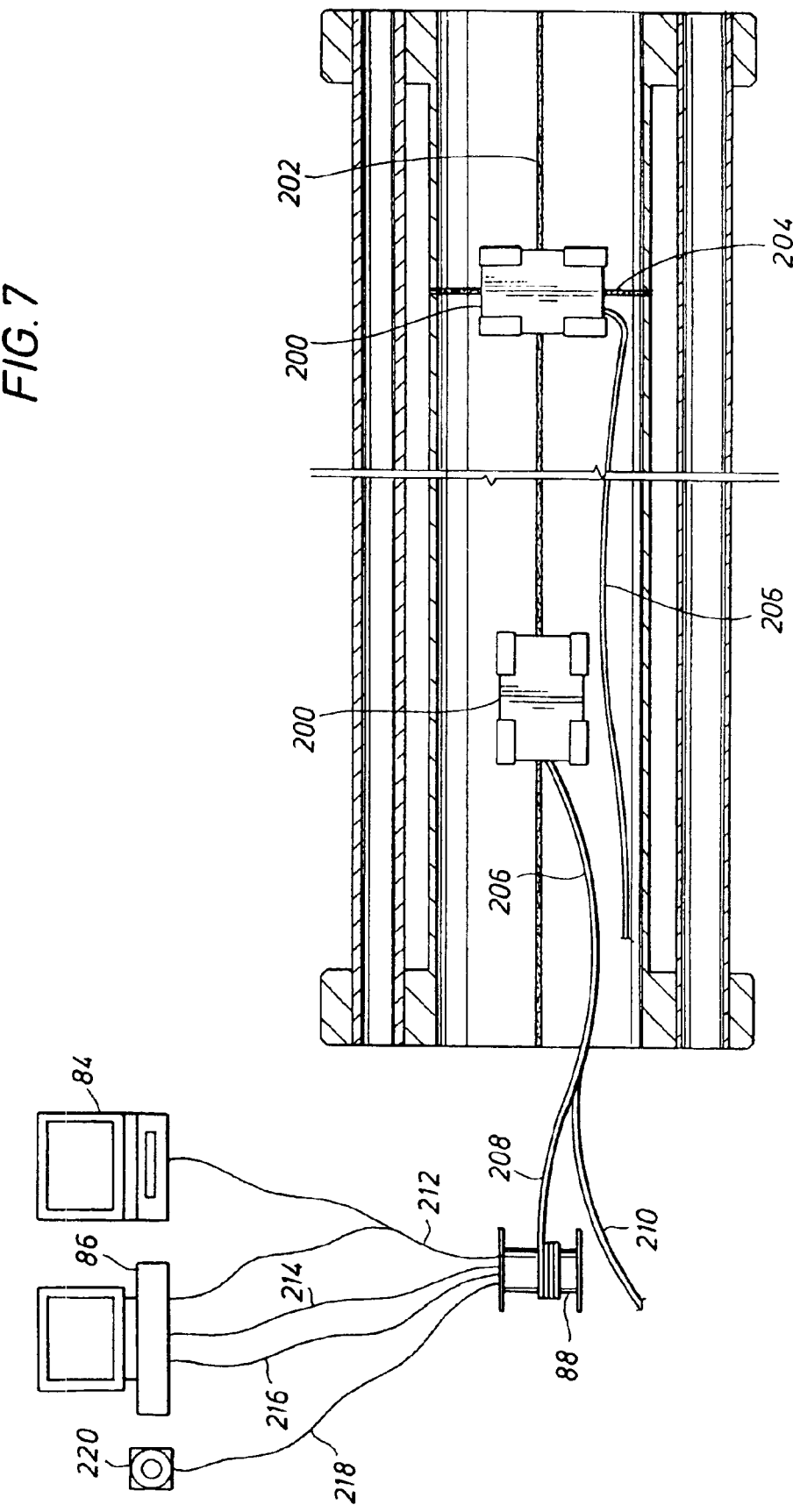
FIG. 7 is a side view in partial section of a preferred system for performing TOFD testing of a large diameter pipe.

FIG. 7 shows a crawler 200 carrying the TOM system in operation. Two such crawlers 200 are shown in FIG. 7, in order to show inspection of a longitudinal weld 202 and a girth weld 204, while the system preferably includes a single crawler. The crawler preferably includes a single umbilical 206, which includes a bi-directional signal cable 208 and a water supply line 210. As previously described, the water supply line 210 provides the water couplant for the TOM transducers. The signal cable 208 is preferably taken up on the take-up reel 88 to keep the slack out of the signal cable 208 during the inspection.

The signal cable includes a number of lines, including a video signal line 212 from the on-board camera to the television and video cassette recorder 84 and the computer 86 to provide real time viewing of the camera view and to provide a record of the inspection. The signal cable 208 further includes a signal line 214 from the encoder for precise position measurement and indication, a signal line 216 for carrying the TOM signal to the computer, and a maneuvering control signal line 218 from a remote, joystick control 220.

In operation, the crawler 200 is driven down the pipe, and the operator views the interior of the pipe at the television monitor 84, controlling the movement of the crawler with the joystick control 220. When a girth weld 204 is encountered, the crawler is turned and driven around the circumference of the pipe.

Figure 8B:
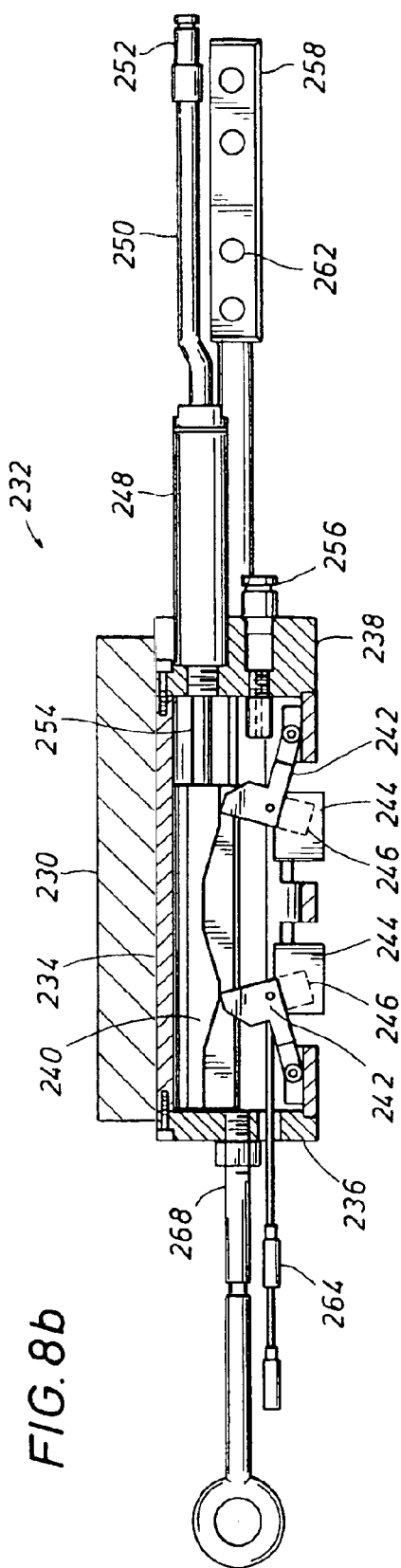
Figure 8C:
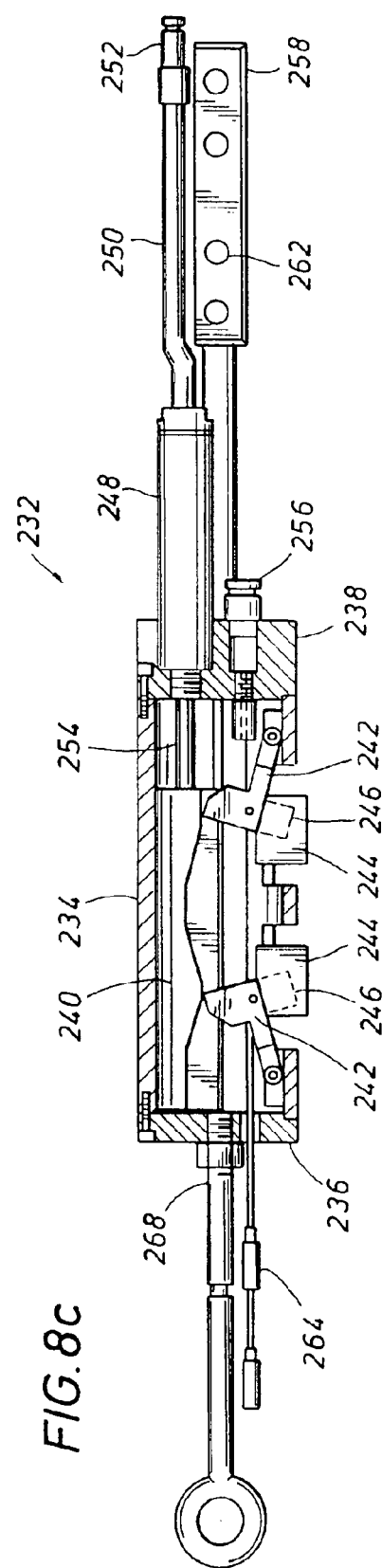

FIG. 8a depicts the arrangement for the performance of TOM testing in smaller tubulars in accordance with this invention. FIGS. 8b and 8c depict the tools of the invention for conducting TOFD testing in 4" and 3" nominal ID tubulars, respectively. The tools are identical, with the exception of an adapter sleeve 230 to adapt the tool to the larger 4" ID tubular. Thus, the following description will apply to both FIGS. 8b and 8c.

A TOM tool 232 comprises a body 234, a left end cover 236, and a right end cover 238. Within the body is a carrier and slide assembly 240, which provides a cam action for a set of yokes 242. The yokes support a set of shoes 244 in which are mounted the TOM transducers 246. The shoes 244 are shown in FIGS. 8b and 8b in the deployed position in order for the shoes to make contact with the interior surface of the small tubular in preparation for the TOM test. The carrier and slide assembly 240 is moved transversely by air pressure from an air cylinder 248 which is supplied from a nipple 250 and air connection 252. Actuation or retraction of a rod 254 from the air cylinder moves the carrier and slide assembly 240 back and forth, so that the yokes ride up and down on the slides, deploying and retracting the shoes.

The body also retains a connector 256 for a water connection. The water from the water connection, as previously described, serves as a couplant for the TOM signal. The body is firmly connected to a drive arm 258 which provides a means for rotating the tool 232 in a rotary motion for complete circumferential coverage of the TOM test. The drive arm 258 is preferably connected to a square tube drive means 260 (FIG. 8a) by removable screws 262. At the opposite end of the body is a signal cable connector 264 for connecting the tool to the computer, preferably by way of a pre-amplifier 266 (FIG. 8a). At the same end of the body is an eyebolt connection 268 for pulling the tool through the tubular.

FIG. 8a shows the use of the tool 232 in a small diameter tubular in performing the TOM test. As previously described with regard to the use of other tools, the wire line 18 is coupled to the eyebolt 268 and then back to the winch assembly 12 driven by a winch motor 14 and the winch assembly 12 is adapted for mounting to the flange 16. The wire line 18 is pulled over an idler pulley 98 which contacts the encoder 90 to precisely locate the tool 232 within the tubular. The signal cable 264 is wound to a takeup reel 88 to keep slack out of the cable. At the other end of the tubular are provided the drive means 260, a water supply connection 270 for the water couplant, and an air supply connection 272 for coupling to the connection 252 (FIGS. 8b and 8c).

To use the tool 232, the signal line 264 and the wire line 18 are fed through the tubular and connected to the tool. The air and water connections are made up, and rotating drive means 260 is connected. Then, the tool is registered with the end of the tubular, and the encoder is zeroed. The tool is the pulled through the tubular and rotated by the rotating drive means 260, imaging the tubular for internal flaws. The computer captures the image for later review and analysis.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

We claim:

1. A system for inspecting a tubular comprising:
 a) a corrosion mapping tool, the corrosion mapping tool comprising:
  i) a substantially cylindrical body defining mutually opposed ends;
  ii) a flange on each of the ends of the body;
  iii) a substantially circular seal plate on each flange;
  iv) a pulse echo transducer on the body;
  v) an end plate on the body; and
  vi) a hub on the end plate, the hub including a coupling adapted to receive a water hose connection;
  vii) a water channel in the hub terminating at the coupling;
  xiii) a flexible tube in fluid communication with the water channel; and
  ix) a penetration through the body, wherein the flexible tube is in fluid communication with the penetration, and wherein the water channel, the flexible tube, and the penetration are adapted to carry water to flood an annular chamber defined by the body, the seal plates, and the interior surface of the tubular; and
 b) a drawing system removably coupled to the inspection tool with a wire line, the drawing system adapted to pull the inspection tool through the tubular.

2. The system of claim 1, further comprising an encoder to locate the position of the inspection tool within the tubular.

3. The system of claim 2, wherein, in use, the wire line passes over the encoder, the encoder providing an indication of the position of the inspection tool within the tubular as the wire line passes over it.

4. The system of claim 1, further comprising:
 a) a cable connector on one of the flanges to receive a signal from the transducer; and
 b) a signal cable to connect the cable connector to a computer exterior the tubular.

5. The system of claim 1, wherein the pulse echo transducer comprises a plurality of transducer elements and wherein the plurality of transducer elements are arranged circumferentially around the body.

6. The system of claim 5, wherein the transducer elements provide a 360° coverage of the inside of the tubular.

* * * * *